(12) United States Patent
Barry et al.

(10) Patent No.: US 8,157,854 B2
(45) Date of Patent: Apr. 17, 2012

(54) METHOD AND SYSTEM FOR DELIVERY OF COATED IMPLANTS

(75) Inventors: James J. Barry, Marlborough, MA (US); Sean Gilligan, Claregalway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/837,981

(22) Filed: Jul. 16, 2010

(65) Prior Publication Data
US 2010/0280522 A1 Nov. 4, 2010

Related U.S. Application Data (63) Continuation of application No. 09/842,833, filed on Apr. 27, 2001, now abandoned.

(51) Int. Cl.
*A61F 2/06* (2006.01)
(52) U.S. Cl. .................................................... 623/1.11
(58) Field of Classification Search .................. 623/1.12, 623/1.4–1.54, 1.11, 1.1, 1.13, 1.23; 427/2.24, 427/2.15, 2.1; 606/191–195
See application file for complete search history.

(56) References Cited

U.S. PATENT DOCUMENTS

| | | | | |
|---|---|---|---|---|
| 4,950,227 A | * | 8/1990 | Savin et al. ................... | 623/1.12 |
| 5,147,302 A | | 9/1992 | Euteneuer et al. | |
| 5,342,307 A | | 8/1994 | Euteneuer et al. | |
| 5,409,495 A | | 4/1995 | Osborn | |
| 5,509,899 A | | 4/1996 | Fan et al. | |
| 5,556,383 A | | 9/1996 | Wang et al. | |
| 5,634,928 A | | 6/1997 | Fischell et al. | |
| 5,731,087 A | * | 3/1998 | Fan et al. ....................... | 428/412 |
| 5,733,303 A | | 3/1998 | Israel et al. | |
| 5,792,172 A | | 8/1998 | Fischell et al. | |
| 5,807,520 A | | 9/1998 | Wang et al. | |

(Continued)

FOREIGN PATENT DOCUMENTS
EP 0697226 A1 2/1996
(Continued)

OTHER PUBLICATIONS
European Patent Office, International Search Report in related International Application No. PCT/US02/08649, mailed Jul. 29, 2002.
(Continued)

*Primary Examiner* — Alvin J Stewart
(74) *Attorney, Agent, or Firm* — Kenyon & Kenyon LLP (57) ABSTRACT

Method and system for delivery of coated implants is provided. One embodiment encompasses a coated implant delivery system. This system includes an implant delivery device having a first end, a second end, and an inner lumen, wherein the first end has a releasable implant retention region with an accessible surface having a coated implant adhesion-resistant treatment. In another embodiment a method of deploying a coated releasable implant at a target site of a vessel using an implant delivery system is provided. This method includes inserting a portion of an implant delivery device having a releasable implant into the vessel, advancing the implant delivery device to the target site, deploying the releasable implant from the delivery device, and withdrawing the inserted portion of the implant delivery device from the vessel. The implant delivery device in this embodiment has a releasable implant retention region with an accessible surface having a coated implant adhesion-resistant treatment and wherein the releasable implant has a first coating that faces the accessible surface of the releasable implant retention region.

15 Claims, 5 Drawing Sheets

U.S. PATENT DOCUMENTS

| | | | |
|---|---|---|---|
| 5,843,120 | A | 12/1998 | Israel et al. |
| 5,902,631 | A * | 5/1999 | Wang et al. .................... 427/2.1 |
| 5,947,977 | A | 9/1999 | Slepian et al. |
| 5,980,551 | A | 11/1999 | Summers et al. |
| 5,989,280 | A | 11/1999 | Euteneuer et al. |
| 6,007,545 | A | 12/1999 | Venturelli |
| 6,080,488 | A | 6/2000 | Hostettler et al. |
| 6,096,027 | A | 8/2000 | Layne |
| 6,096,056 | A | 8/2000 | Brown |
| 6,096,070 | A | 8/2000 | Ragheb et al. |
| 6,153,252 | A | 11/2000 | Hossainy et al. |
| 6,156,373 | A | 12/2000 | Zhong et al. |
| 6,218,016 | B1 * | 4/2001 | Tedeschi et al. ........... 428/423.1 |
| 6,221,097 | B1 | 4/2001 | Wang et al. |
| 6,251,136 | B1 | 6/2001 | Guruwaiya et al. |
| 6,270,779 | B1 * | 8/2001 | Fitzhugh et al. .............. 424/400 |
| 6,287,285 | B1 * | 9/2001 | Michal et al. .................. 604/264 |
| 6,306,144 | B1 | 10/2001 | Sydney et al. |
| 6,315,794 | B1 | 11/2001 | Richter |
| 6,331,186 | B1 | 12/2001 | Wang et al. |
| 6,348,060 | B1 | 2/2002 | Brown |
| 6,368,658 | B1 * | 4/2002 | Schwarz et al. ............. 427/2.15 |
| 6,379,691 | B1 * | 4/2002 | Tedeschi et al. .............. 424/423 |
| 6,409,716 | B1 | 6/2002 | Sahatjian et al. |
| 6,656,517 | B2 * | 12/2003 | Michal et al. ................ 427/2.24 |
| 6,682,771 | B2 * | 1/2004 | Zhong et al. ................. 427/2.24 |
| 6,730,349 | B2 * | 5/2004 | Schwarz et al. ............... 427/2.1 |
| 7,247,338 | B2 * | 7/2007 | Pui et al. ...................... 427/2.24 |

FOREIGN PATENT DOCUMENTS

| | | |
|---|---|---|
| JP | 08243170 A | 9/1996 |
| JP | 09500561 T | 1/1997 |
| WO | 9503083 A1 | 2/1995 |
| WO | 9520992 A1 | 8/1995 |
| WO | 0067816 A1 | 11/2000 |

OTHER PUBLICATIONS

Japan Patent Office, Notice of Reasons for Rejection in related Japanese Patent Application No. 2002-584993, mailed Jun. 5, 2007.

* cited by examiner

METHOD AND SYSTEM FOR DELIVERY OF COATED IMPLANTS

This application is a continuation of U.S. Ser. No. 09/842,833, filed Apr. 27, 2001, which is hereby incorporated by reference in its entirety.

TECHNICAL FIELD

The present invention regards method and system for delivering coated medical implants. More specifically the present invention regards treating at least a portion of the surface of a medical delivery device to inhibit damage to the coating of a releasable implant delivered by the medical delivery device.

BACKGROUND OF THE INVENTION

The positioning and deployment of medical implants is a common often-repeated procedure of modern medicine. Medical implants may be used for innumerable medical purposes including the reinforcement of recently re-enlarged lumens and the replacement of ruptured vessels. These implants may be delivered by securing them to the distal end of a delivery device, positioning the distal end of the device near a target delivery site, and then deploying the implant from the device to its desired position. The implant may be deployed by inflating the distal end of the device or through other forces that urge the implant from the device's distal end. When the implant has been coated this coating is susceptible to being damaged or completely removed from the implant during the deployment process—an unwanted result.

The mechanical process of deploying the implant often exerts significant shearing and adhesional forces on and against the surface of the coating of the implant. These forces can strip, damage or otherwise deplete the amount of coating on the implant. When the amount of coating is depleted the implant's effectiveness may be compromised and additional risks may be inured into the procedure. For example, when the coating of the implant includes a therapeutic, if some of the coating were removed during deployment, the therapeutic may no longer be able to be administered to the target site in a uniform and homogenous manner. Thus, some areas of the target site may receive high quantities of therapeutic while others may receive low quantities of therapeutic. Similarly, if the therapeutic is ripped from the implant it can reduce or slow down the blood flowing past it, thereby, increasing the threat of thrombosis or, if it becomes dislodged, the risk of embolisms.

The delivery of expandable stents, stent grafts, and aneurysm coils are specific examples of medical procedures that involve the deployment of coated implants. Expandable stents are tube-like medical devices designed to support the inner walls of a lumen within the body of a patient. These stents are typically positioned within a lumen of the body and, then, expanded to provide internal support for the lumen. They may be self-expanding or, alternatively, may require external forces to expand them. In either case they are typically deployed through the use of a catheter of some kind. These catheters will typically carry the stent at their distal end.

Because of the direct contact of the stent with the inner walls of the lumen, stents have been coated with various compounds and therapeutics to enhance their effectiveness. These coatings may, among other things, be designed to facilitate the acceptance of the stent into its applied surroundings and to facilitate the delivery of therapeutic to the target site. When this coating is haphazardly applied or has somehow been removed during the stent's manufacture or delivery the stent's effectiveness can be compromised.

In certain circumstances faulty or ineffectively deployed stents can require the removal and reinsertion of the stent through a second medical procedure. For example, as the balloon at the distal end of the stent is inflated, to expand and position the stent, frictional shear forces are created between the surface of the catheter and the stent coating. These frictional surface shear forces, as well as the adhesional forces between the coating and the stent, act to tear away or unevenly redistribute the stent coating. Thus, the physical forces used to deliver the stent can create an abating result that reduces the overall effectiveness of a deployed coated stent.

SUMMARY OF THE INVENTION

Method and system for delivery of coated implants is provided. One embodiment encompasses a coated implant delivery system. This system includes an implant delivery device having a first end, a second end, and an inner lumen, wherein the first end has a releasable implant retention region with an accessible surface that has a coated implant adhesion-resistant treatment.

In another embodiment a method of deploying a coated releasable implant at a target site of a vessel using an implant delivery system is provided. This method includes inserting a portion of an implant delivery device having a releasable implant into the vessel, advancing the implant delivery device to the target site, deploying the releasable implant from the delivery device, and withdrawing the inserted portion of the implant delivery device from the vessel. The implant delivery device in this embodiment has a releasable implant retention region with an accessible surface having a coated implant adhesion-resistant treatment and wherein the releasable implant has a first coating that faces the accessible surface of the releasable implant retention region.

DETAILED DESCRIPTION

Figure 1:
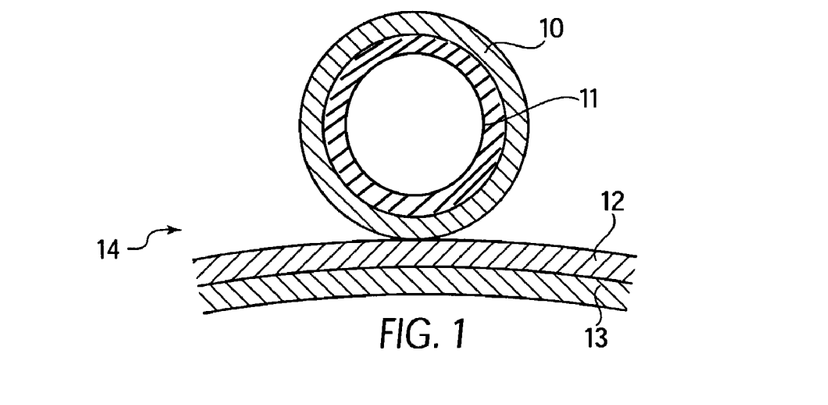
FIG. 1 is an enlarged cross-sectional view of a coated support from a coated implant in contact with an implant delivery device prior to the release of the implant from the implant delivery device in accord with an embodiment of the present invention.
Figure 2:
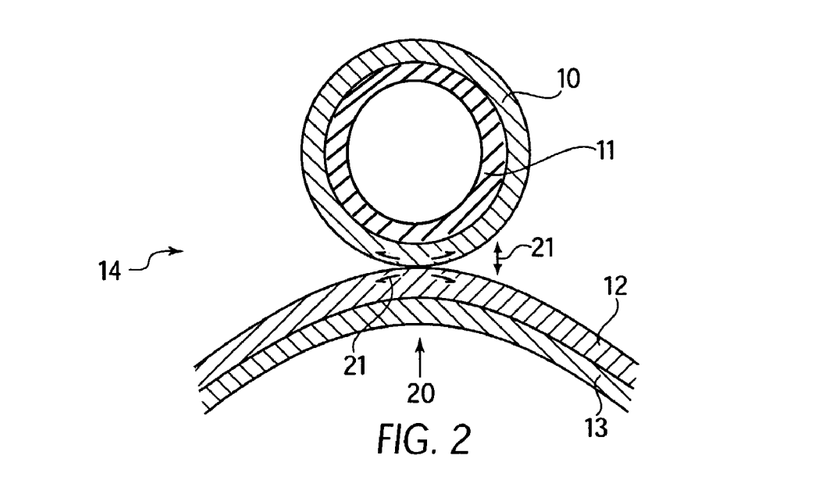
FIG. 2 is an enlarged cross-sectional view of a coated support from a coated implant in contact with an implant delivery device during the release of the implant from the implant delivery device in accord with an embodiment of the present invention.
Figure 3:
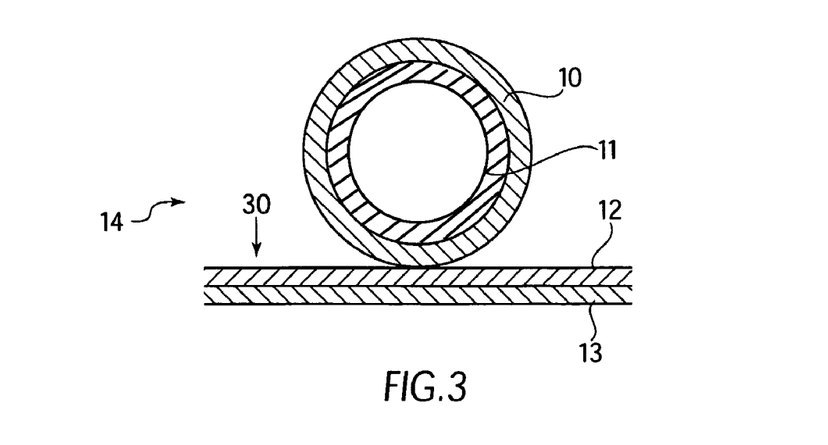
FIG. 3 is an enlarged cross-sectional view of a coated support from a coated implant after it has been released from the implant delivery device in accord with an embodiment of the present invention.

FIGS. 1-3 provide a sequential illustration of an enlarged sectional view of a single support of a coated medical implant before its deployment, during its deployment and after its deployment in accord with one embodiment of the present invention. This medical implant may be any one of numerous medical implants including coated stents, coated stent grafts, and aneurysm coils. These implants, as well as others, may be carried to a target site within the body by a medical device and then deployed in order to provide medical relief to the targeted site.

FIG. 1 provides an enlarged cross-section of one support of an implant carried by an implant delivery device 14 to a target site within the body of a patient. As can be seen in FIG. 1, the coating 10 of the coated support 11 is in contact with the adhesion resistant treatment 12 of the implant retention region 13 of the implant delivery device 14. As is evident, the coating 10 completely encircles the coated support 11. This support is one of many supports that may comprise the coated implant. These supports may have various cross-sectional areas in addition to the circular cross-section illustrated in this embodiment. The other supports for this implant are not shown due to the enlarged scale of the figure.

FIG. 2 provides a similar enlarged cross-section. In this cross-section, however, the implant is in the process of being deployed from the implant delivery device 14. Here, the implant deliver device 14 is expanding, as shown by arrow 20, and urging the implant towards the target site (not shown). As the implant is urged upwards, shear forces and normal forces, represented by arrows 21, are developed between the coating 10 of the support 11 and the adhesion resistant treatment 12. Because the adhesion resistant treatment 12 creates little if any static, dynamic, friction or other adhesional forces with the coating 10, the severity of these shear and normal forces is dramatically reduced. Consequently, rather than having the coating 10 ripped from the individual supports as the implant is deployed the coating 10 is able to slip or slide over the expanding implant retention region 13 of the implant delivery device 14 and, thus, may remain over the support 11.

FIG. 3 provides a view of the same support 11 and delivery device 14, this time after the implant has been deployed. As is evident, the coating 10 has remained intact on the support 11 of the implant. Thus, due to the adhesion resistant treatment 12, the frictional forces generated during the delivery of the implant are reduced to the extent that they may no longer present a substantial threat to removing or otherwise tearing the coating 10 from the individual supports 11 of the coated implant.

The adhesion resistant treatment may be one of numerous available treatments. It may be a silicone applied directly to the implant retention region 13 of the implant delivery device 14. It may also be a hydrogel, a carbowax, a polyethylene oxide (PEO), a polyacrylic acid (PAA), a polythlene glycol (PEG) and any other material that can significantly reduce the separating forces generated during the delivery of the implant. Alternatively, the adhesion resistant treatment may be a specific treatment performed directly on the implant retention region 13 of a delivery device 14. For example, the region may be buffed or polished to create a super slick or super smooth region that develops little if any static or dynamic frictional forces during the delivery of the implant. Moreover, in addition to resisting adhesion, the treatment may also affirmatively repel the coating of the implant. For example, should the implant coating be repelled by certain compounds these compounds may be embedded or otherwise impregnated into or on the implant retention region 13 of the delivery device to facilitate the proper deployment of the implant.

The implant adhesion-resistant treatment may also contain a therapeutic that can facilitate the treatment of the target site or a tracer chemical to assist a physician in positioning or otherwise deploying the implant.

This therapeutic can include pharmaceutically active compounds, nucleic acids with and without carrier vectors such as lipids, compacting agents (such as histones), virus (such as adenovirus, andenoassociated virus, retrovirus, lentivirus and a-virus), polymers, hyaluronic acid, proteins, halifuginone, cells and the like, with or without targeting sequences.

Other specific examples of therapeutics used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, COX-2 inhibitors, and mesalamine; calcium entry blockers such as verapamil, diltiazem and nifedipine; antineoplastic/antiproliferative/anti-mitotic agents such as paclitaxel and derivatives, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

FIGS. 4-7 furnish various side and sectional views of an implant delivery device, system, and implant in accord with alternative embodiments of the present invention. In these embodiments the implant delivery device may be an inflatable balloon catheter and the implant may be an expandable stent.

Figure 4:
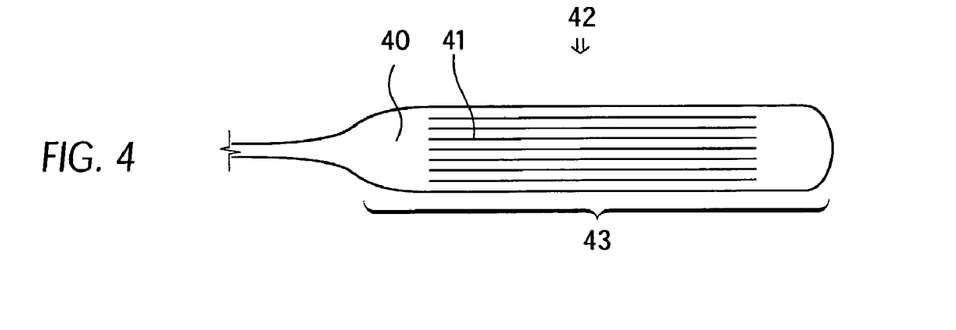
FIG. 4 is a side view of the implant retention region of an implant delivery device having an adhesion-resistant treatment in accord with an alternative embodiment of the present invention.

FIG. 4 is a side view of an implant delivery device 42, having a releasable implant retention region 40 and a coated implant adhesion resistant treatment 41. The adhesion resistant treatment 41 in this embodiment may be silicone, although it may also be a hydrophilic, a PEO and a PAA. The delivery device 42 in this embodiment may be a balloon catheter having an expandable balloon tip 43. The balloon tip 43 may be sized both in its length and circumference to accommodate the implant during its loading onto the implant retention region, through its positioning near the target site, and during its delivery to the target site.

Figure 5:
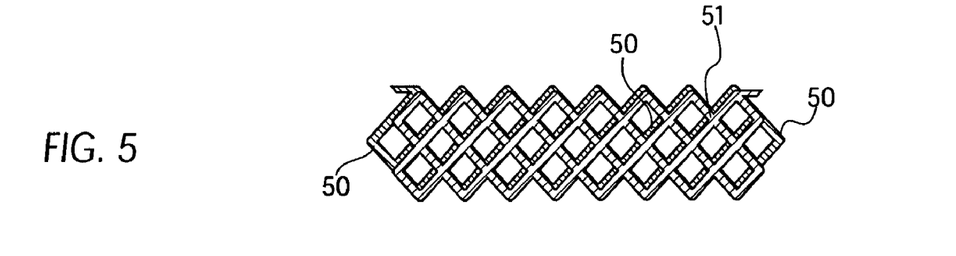
FIG. 5 is a side perspective view of a coated releasable implant as employed in an alternative embodiment of the present invention.

FIG. 5 is a side perspective view of an expandable stent 51. The individual supports comprising this stent are covered with a coating 50.

Figure 6:
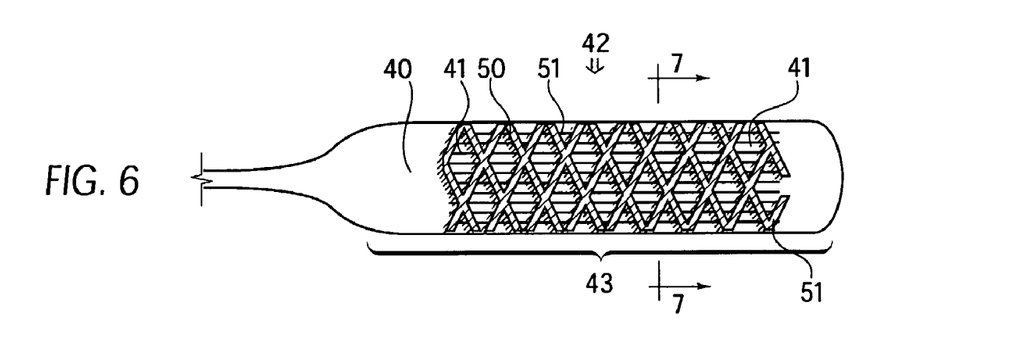
FIG. 6 is a side view of an implant delivery system in accord with an alternative embodiment of the present invention.

FIG. 6 is a side view of the entire stent delivery system. Here, the stent 51 is mounted in the implant retention region 40 of the implant delivery device 42. In use the implant delivery device 42 may be guided down a lumen of the body and positioned near a target site of the body. Then, after being properly positioned by a practitioner performing the procedure, the balloon tip 43, having an implant retention region 40, may be expanded to expand and stretch the stent 51 to permit it to become lodged in the lumen in order to begin to provide support to the lumen. Once deployed, with its coating intact, substantially due to the adhesion resistant treatment 41, the catheter 42 may be removed from the target area.

Figure 7:
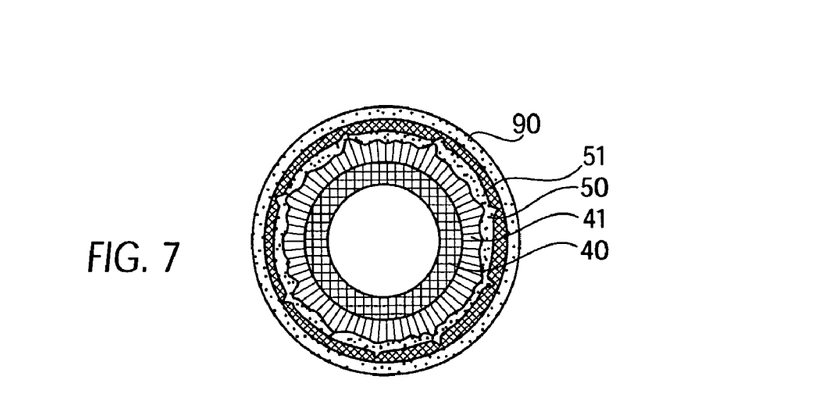
FIG. 7 is a cross-sectional view taken along the line 7-7 of FIG. 6.

FIG. 7 presents a cross-sectional view of the delivery system taken along line 7-7 of FIG. 6. Clearly evident in this figure are the implant retention region 40, the adhesion resistant treatment 41, stent coating 50, and stent 51. As can be seen in this illustration the coating 50 is both inside and outside of the stent 51.

Figure 8:
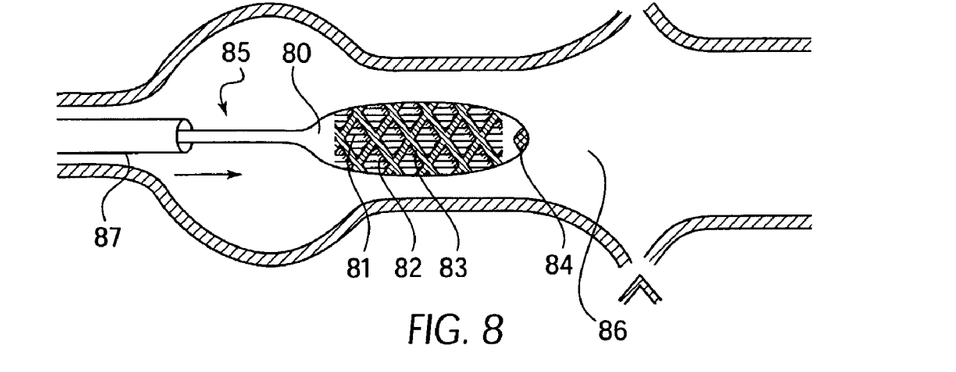
FIG. 8 is a side view of an implant delivery system as employed in accord with an alternative embodiment of the present invention.
Figure 9:
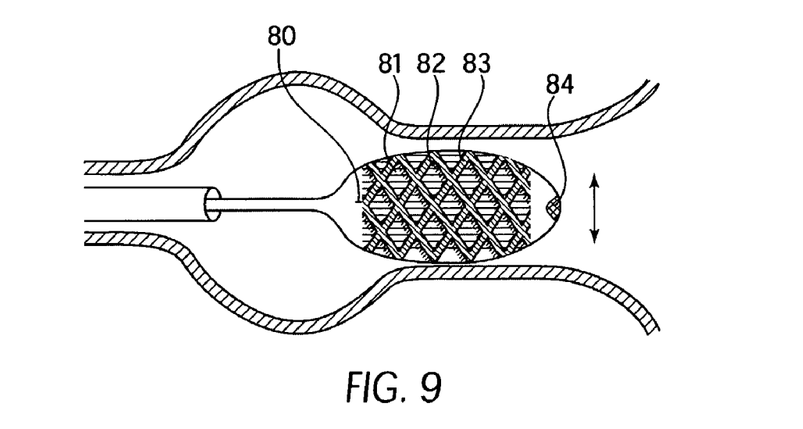
FIG. 9 is a side view of an implant delivery system as employed in accord with an alternative embodiment of the present invention.
Figure 10:
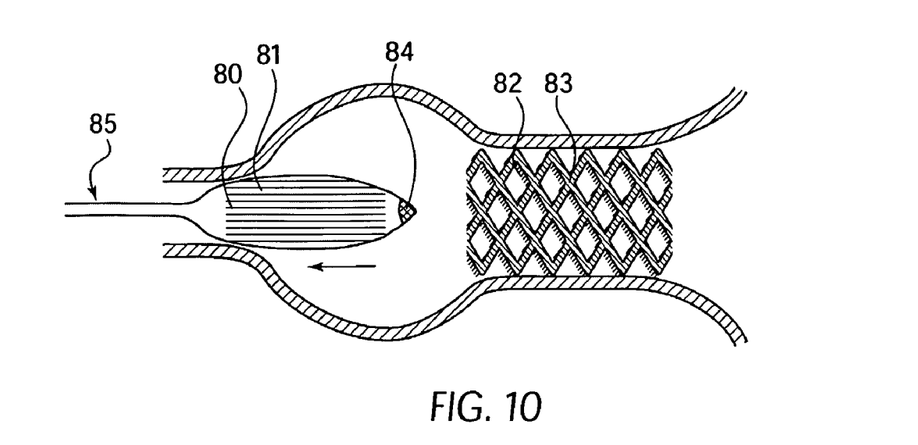
FIG. 10 is a side view of an implant delivery system as employed in accord with an alternative embodiment of the present invention.

FIGS. 8-10 present a sequential deployment sequence of an expandable stent in accord with another alternative embodiment of the present invention. In this embodiment a stent 83 is sought to be deployed within a target site 86. Visible in FIG. 8 are an endoscope 87, an implant delivery device 85, an implant retention region 80, stent 83, a stent coating 82, an insertion coating 84, and a coated implant adhesion resistant treatment 82.

After positioning the distal end of an endoscope 87 near the desired target site 86 the delivery system is urged from the endoscope into the targeted site 86. Here, the most distal tip of the delivery device 85 is treated with a coating to facilitate its smooth insertion through the endoscope 87 and into the target site 86. Once deployed, the device will be inflated as shown in FIG. 9 and will then be removed from the target area as shown in FIG. 10. As can be seen in FIG. 10, the coating on the implant has remained on the inside and outside surface of the stent 83 and was not errantly removed during the inflation of the retention region or the deployment of the stent 83. In addition to treating the distal tip of the endoscope 87, the tube-like longitudinal walls of the delivery device may also be coated to further assist the movement of the device 85 through the endoscope 87.

Figure 11:
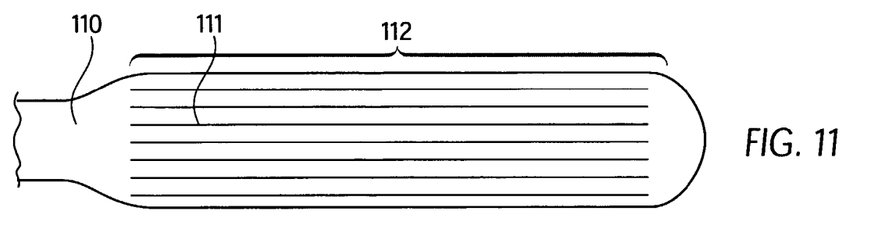
FIG. 11 is a side view of an implant delivery device in accord with an alternative embodiment of the present invention.

FIGS. 11-14 provide yet another alternative embodiment of the present invention. FIG. 11 illustrates a delivery device 110 having an implant retention region 112 that has been treated with a treatment.

Figure 12:
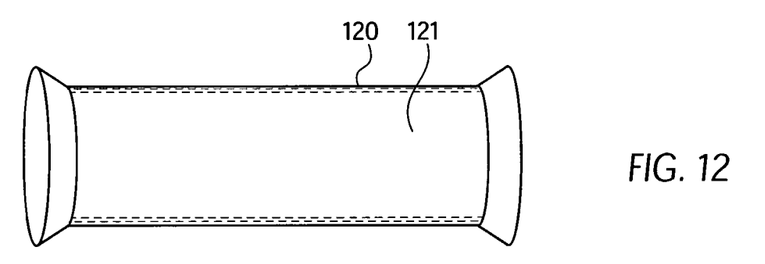
FIG. 12 is the side view of a coated stent graft as employed in accord with an alternative embodiment of the present invention.

FIG. 12 illustrates a stent graft 121 employed in this embodiment. Stent grafts generally may be employed in various regions of the body. They may be used as a bridge for ruptured or dilated vessels. Like the stents described above, they may be coated, and like the stent above, this coating is susceptible to being striped away during its delivery. Thus, in this embodiment, the retention region 112 of the delivery device has been treated with an adhesion resistant treatment 111 to resist adhesion between it and the coating of the stent graft 121.

Figure 13:
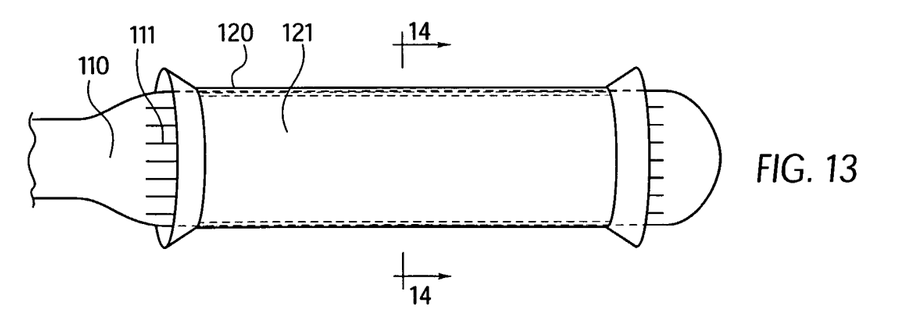
FIG. 13 is the side view of an implant delivery system in accord with an alternative embodiment of the present invention.
Figure 14:
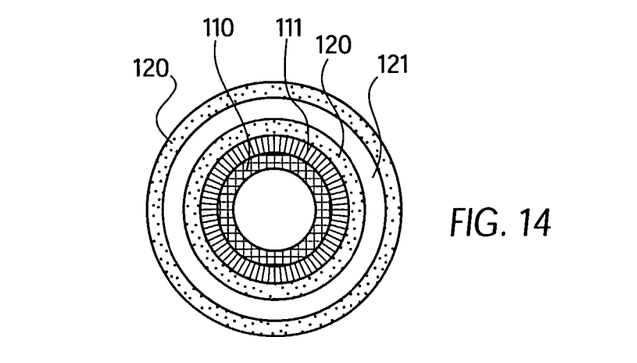
FIG. 14 is a cross-sectional view taken along the line 14-14 of FIG. 13.

FIG. 14, a cross-section taken along line 14-14 of FIG. 13, clearly shows the interface between the coating 120 of the stent graft 121 and the adhesion resistant treatment 111 of the delivery device 110. In use, like the above embodiments, this coating 120 will more likely remain and not be striped or otherwise removed from the implant due to its interface with the adhesion resistant treatment 111.

Figure 15:
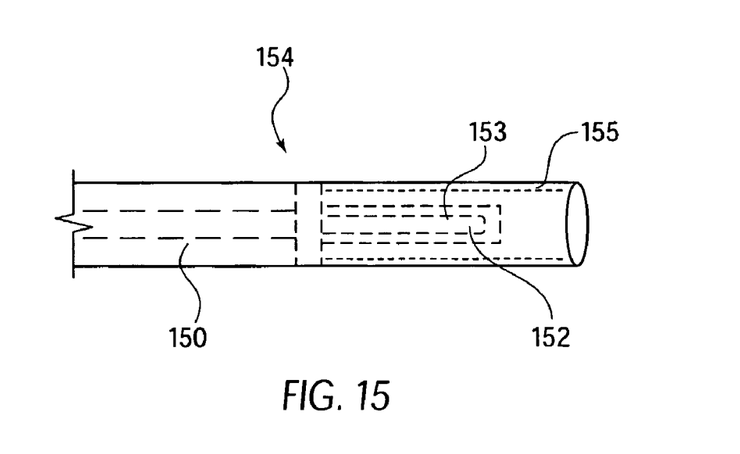
FIG. 15 is a side view of an implant delivery system in accord with an alternative embodiment of the present invention.
Figure 16:
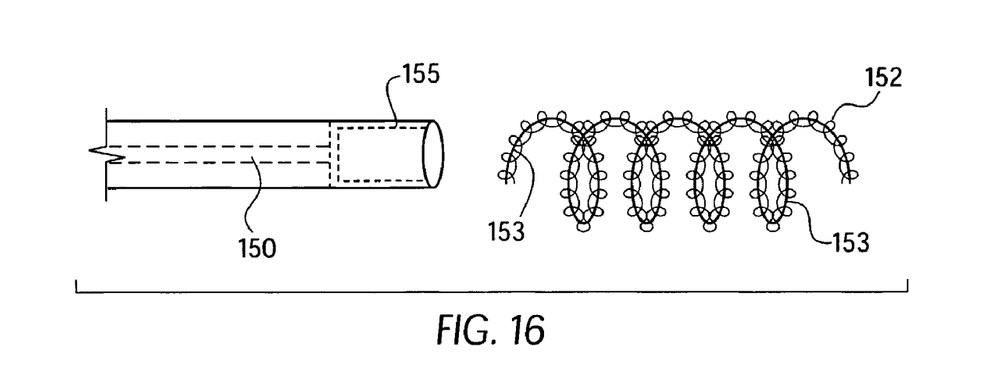
FIG. 16 is a side view of the implant delivery system of FIG. 15 after having deployed an aneurysm coil in accord with an alternative embodiment of the present invention.

FIGS. 15-16 provide an implant delivery system in accord with another alternative embodiment of the present invention. The delivery unit 154 in this embodiment stores an aneurysm coil 152 for deployment within the body. Rather than having the implant surrounding the delivery device as in the previous embodiments the implant is contained within the delivery device in this embodiment.

Illustrated in FIGS. 15 and 16 are the delivery device 150, an internal plunger 151, an undeployed aneurysm coil 152, a deployed aneurysm coil 162, and a coating 153. Rather than treating the outside of the delivery device as in the other embodiments, the inside the delivery device 154 is treated with an adhesion resistant treatment 155. Like the other embodiments, however, this accessible treatment reduces the risk of tearing or otherwise removing the coating from the implant before and after its deployment. In this embodiment the implant coating 153 is shown on the aneurysm coil while the coil is straight and within the delivery device 154 and after it is deployed and has curled in reaction to the temperature of its new surroundings. By treating the delivery device 154 the coating 153 can remain intact and be available to treat the ailing lumen in contact with the coil 152.

Figure 17:
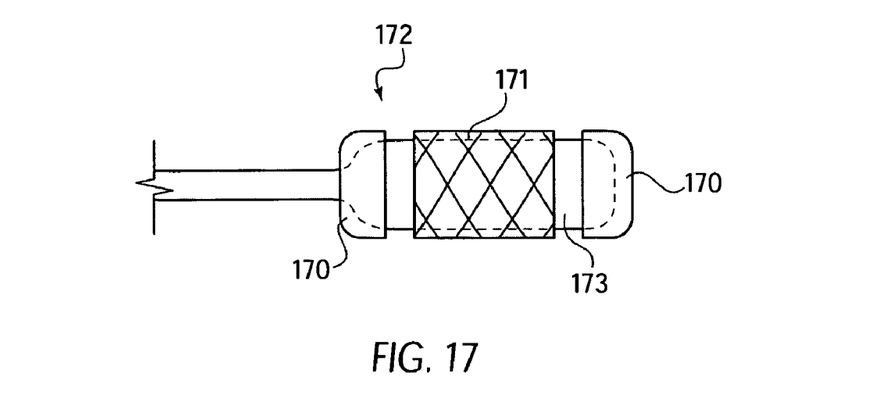
FIG. 17 is a side view of an implant delivery system in accord with an alternative embodiment of the present invention.

FIG. 17 provides a side view of an implant delivery system in accord with another alternative embodiment of the present invention. In FIG. 17 the distal end of a delivery device 172 is shown having an expandable stent 171 on its implant retention region 173 as well as two caps or SOX 170 which are positioned and placed to retain the stent 171 in place during the positioning of the distal end of the device near the target site. By placing and locking these caps or SOX 170 on the delivery device 172 the stent 171 may be locked in place and not placed at risk of becoming deployed prematurely, prior to the final positioning of the distal end of the delivery device 172. Once positioned, the deliver device 172 may be expanded without severe constraint from these SOX which may either tear away or simply fall off when the implant, retention region 173 begins to expand.

Method and system for delivery of coated implants is provided. The above-described embodiment are illustrative examples of the present invention. As will be evident to one of skill in the art modifications to these embodiments as well as entirely new embodiments are plausible without departing from the spirit and scope of the present invention.

What is claimed is:

1. A coated implant delivery system comprising:
an implant delivery device having a distal end with a releasable implant retention region, the releasable implant retention region having an outer surface comprising a delivery device coating, said delivery device coating including a therapeutic agent; and
a releasable implant having an implant coating, the implant coating facing the delivery device coating, and the releasable implant releasably positioned in physical communication with the releasable implant retention region, the implant coating being positioned on an inner surface and an outer surface of the implant and including a therapeutic agent.

2. The coated implant delivery system of claim 1 wherein the implant delivery device is a balloon catheter.

3. The coated implant delivery system of claim 1 further comprising two sleeves positioned in physical communication with the releasable implant retention region.

4. The coated implant delivery system of claim 1 wherein the delivery device coating comprises an implant adhesion-resistant treatment.

5. The coated implant delivery system of claim 4 wherein the implant adhesion-resistant treatment includes a non-adhesive silicone coating.

6. The coated implant delivery system of claim 4 wherein the implant adhesion-resistant treatment includes a non-adhesive hydrophilic coating.

7. The coated implant delivery system of claim 4 wherein the implant adhesion-resistant treatment includes a non-adhesive hydrogel coating.

8. The coated implant delivery system of claim 4 wherein the implant adhesion-resistant treatment includes a non-adhesive carbowax coating.

9. The coated implant delivery system of claim 4 wherein the implant adhesion-resistant treatment includes a non-adhesive PEO coating.

10. The coated implant delivery system of claim 1 wherein the releasable implant is a balloon-expanding stent.

11. The coated implant delivery system of claim 1 wherein the releasable implant is a self-expanding stent.

12. The coated implant delivery system of claim 1 wherein the releasable implant is a graft.

13. The coated implant delivery system of claim 1 wherein the releasable implant is an aneurysm coil.

14. The coated implant delivery system of claim 1, wherein the coated implant adhesion-resistant treatment reduces shear and normal friction between the releasable implant and the implant delivery device.

15. The coated implant delivery system of claim 1, wherein said releasable implant retention region extends along an entire length of the implant.

* * * * *